United States Patent
Joshi et al.

(10) Patent No.: US 9,326,785 B2
(45) Date of Patent: May 3, 2016

(54) CONNECTOR FOR A LAPAROSCOPIC SURGICAL SYSTEM

(75) Inventors: Sharad H. Joshi, Hopkinton, MA (US); Jean-Luc Boulnois, Boston, MA (US); Chris A. Devlin, Wakefield, MA (US); Peter Aliski, Malden, MA (US); Russ LaRoche, Salem, NH (US); Chris Sullivan, Grafton, MA (US)

(73) Assignee: MICROLINE SURGICAL, INC., Beverly, MA (US)

( * ) Notice: Subject to any disclaimer, the term of this patent is extended or adjusted under 35 U.S.C. 154(b) by 249 days.

(21) Appl. No.: 13/466,425

(22) Filed: May 8, 2012

(65) Prior Publication Data

US 2012/0289773 A1    Nov. 15, 2012

Related U.S. Application Data

(60) Provisional application No. 61/485,263, filed on May 12, 2011.

(51) Int. Cl.
*A61B 17/00* (2006.01)
*A61B 17/29* (2006.01)
*A61B 19/00* (2006.01)

(52) U.S. Cl.
CPC ........... *A61B 17/29* (2013.01); *A61B 2017/294* (2013.01); *A61B 2017/2931* (2013.01); *A61B 2017/2948* (2013.01); *A61B 2019/4873* (2013.01)

(58) Field of Classification Search
CPC ............. A61B 17/29; A61B 2017/294; A61B 2017/2931; A61B 2017/2948; A61B 2019/4873
See application file for complete search history.

(56) References Cited

U.S. PATENT DOCUMENTS

| | | | |
|---|---|---|---|
| 2,002,121 A * | 5/1935 | McMaster | 29/416 |
| 3,245,703 A * | 4/1966 | Manly | 285/319 |
| 4,330,144 A * | 5/1982 | Ridenour | 285/382.5 |
| 4,842,548 A * | 6/1989 | Bolante | 439/461 |
| 5,431,667 A | 7/1995 | Thompson et al. | |
| 5,810,879 A | 9/1998 | de Guillebon | |
| 6,004,417 A * | 12/1999 | Roesch et al. | 156/155 |
| 6,331,165 B1 | 12/2001 | Turturro et al. | |
| 6,406,470 B1 * | 6/2002 | Kierce | 604/535 |
| 6,494,877 B2 * | 12/2002 | Odell et al. | 606/1 |
| 6,595,984 B1 * | 7/2003 | DeGuillebon | 606/1 |
| 6,676,874 B1 * | 1/2004 | Muller | 264/249 |
| 6,926,676 B2 | 8/2005 | Turturro et al. | |

(Continued)

FOREIGN PATENT DOCUMENTS

| JP | 2009-226213 | 10/2009 |
|---|---|---|
| WO | 99/59475 | 11/1999 |
| WO | 2010/114634 | 10/2010 |

OTHER PUBLICATIONS

Japan Office action, dated Jul. 16, 2013 along with an english translation thereof.

*Primary Examiner* — Gary Jackson
*Assistant Examiner* — Boniface N Nganga
(74) *Attorney, Agent, or Firm* — Greenblum & Bernstein, P.L.C.

(57) ABSTRACT

A connector for connecting an instrument tip with a laparoscopic tube end, the connector including a base forming a body of the connector, the base having a lumen configured to accommodate an instrument tip actuator therein, and a seal permanently bonded to an inner surface of a proximal end of the base and configured to deform upon connection of the connector with the tube end.

33 Claims, 8 Drawing Sheets

(56) References Cited

U.S. PATENT DOCUMENTS

| | | |
|---|---|---|
| 7,297,121 B2 | 11/2007 | Turturro et al. |
| 7,367,973 B2 * | 5/2008 | Manzo et al. .................... 606/41 |
| 7,862,553 B2 | 1/2011 | Ewaschuk |
| 2002/0029006 A1 | 3/2002 | Turturro et al. |
| 2004/0267297 A1 * | 12/2004 | Malackowski ................ 606/167 |
| 2005/0242528 A1 * | 11/2005 | Nikonchuk ................... 277/628 |
| 2005/0245841 A1 | 11/2005 | Turturro et al. |
| 2007/0027447 A1 * | 2/2007 | Theroux et al. ................. 606/41 |
| 2007/0073247 A1 * | 3/2007 | Ewaschuk ..................... 604/264 |
| 2007/0074762 A1 | 4/2007 | Menn |
| 2007/0078483 A1 * | 4/2007 | Ewaschuk et al. ............ 606/205 |
| 2007/0088351 A1 | 4/2007 | Ewaschuk et al. |
| 2009/0088747 A1 * | 4/2009 | Hushka et al. .................. 606/51 |
| 2009/0240274 A1 * | 9/2009 | Boebel et al. ................. 606/174 |
| 2011/0156352 A1 * | 6/2011 | Bond et al. ..................... 277/312 |
| 2012/0083778 A1 | 4/2012 | McGaffigan et al. |

* cited by examiner

CONNECTOR FOR A LAPAROSCOPIC SURGICAL SYSTEM

CLAIM FOR PRIORITY

This application claims the benefit of priority to U.S. Provisional Application No. 61/485,263, field May 12, 2011, the contents of which are expressly incorporated by reference herein.

BACKGROUND

1. Field of the Invention

This invention relates to an instrument including an electrosurgical apparatus, such as a laparoscopic tube end used for performing laparoscopic, pelvoscopic, arthroscopic, thoroscopic and/or similar such procedures, and more particularly to an electrosurgical apparatus having a connector for fluidically sealing, isolating and electrically insulating a detachable tip when engaged with a laparoscopic tube end.

2. Background of the Invention

Medical procedures such as laparoscopy and the like, which employ a tip at the end of a tube for insertion into the patient, are beneficial because the incisions necessary to perform them are minimal in size, therefore promoting more rapid recovery and lower costs. For example, a patient who undergoes laparoscopic surgery may typically return to normal activity within a period of a few days to about a week, in contrast to more invasive procedures requiring a relatively larger incision (which may require about a month for recovery). Although the term "laparoscopic" is typically used hereinafter, such use of the term "laparoscopic" should be understood to encompass any such similar or related procedures such as, for example, arthroscopic, endoscopic, pelvoscopic and/or thoroscopic or the like, in which relatively small incisions are used.

However, when a tip is detachably connected to the tube end of a laparoscopic device, complications may occur if fluid breaches the connection and enters the interior of the tip or tube end. For example, septic contamination may arise in the laparoscopic device and/or electrical current may unintentionally leak therefrom. After each laparoscopic procedure, the device is also exposed to brushing, chemicals for cleaning and/or sterilization by various methods which may include heating, cooling, and flushing with additional chemicals. The seal in the handpiece may degrade to the point where it loses its integrity (either over use of hundreds of cycles, or from handpiece abuse; which can result in unintended cautery causing damage and injury to structures around a surgical site).

The practice of reprocessing and reusing single-use devices (SUDs) has become increasingly more common because of costs savings and the reduction in waste. However, reprocessed SUDs, such as cutting blades, often do not function as well as SUDs that have not been reprocessed. For example, in the case of reprocessing a cutting blade, the blade may be dulled during the surgical procedure or may be damaged during the reprocessing process such that the cutting blade no longer cuts or opens and closes with the desired or required precision. Further, due to the extensive nooks and crannies, SUD's often cannot be thoroughly sterilized. Therefore, a reprocessed tip, such as those including a cutting blade, may not operate as well after reprocessing any may even result in harm to the patient. Therefore, it is possible that any subpar operation of the reprocessed tip may be incorrectly attributed to the original manufacturer of the reprocessed tip, which may result in damage to the reputation of the original manufacturer.

FIG. 1 shows a tube end 11 of a reusable handpiece 200 to which a conventional tip (which may be a SUD) 20 may be removably attached. The tip has an end effector 202 in the form of a scissors, grasper and the like. The tube end 11 distally extends from a tube 61, which in turn distally extends from the handpiece having handles (or other suitable controls, not shown, for actuating the tip 20) operable by the medical personnel or physician performing the surgery. The tube end 11 includes an elastomeric tube end seal 15, which is typically made from EPDM (ethylene propylene diene monomer). It is often difficult for users to detect when a seal 15 has worn to the point where integrity has been lost. Once integrity is lost, collateral damage can occur any time electrosurgical energy is applied to the device. In the illustrated device, the laparoscopic surgical tip 21 is assembled to the tube of the handpiece 200 using a dual-threaded threaded connector. In other words, the tip 20 includes a yoke 150 having external threading 551, which engages complementary internal threading on an actuation rod (not shown) extending along the length of the tube 61 (thereby providing for the actuation of the end effector), and a back hub 400 includes internal threading (not shown) which engages complimentary external threading 21 on the tube end 11 to secure the back hub to the tube 61. Such an attachment typically creates a 50 pound load on the attached components. The seal 15 on the handpiece 200 is compressed by the back hub to create a barrier for electricity and fluids. FIG. 2 shows an surgical tip affixed to a handpiece 200 of FIG. 1 with a heat shrink 25.

FIG. 3 illustrates a laparoscopic device in which, rather than a seal 15, a piece of flared heat shrink 25 is used on the disposable tip 20 to create a seal with the tube 61. Also, the device of FIG. 3 does not use the dual-threaded design of FIGS. 1-2, but instead uses a single threaded connection (between the tube end and the back hub) and a ball 41-and-clevis arrangement to connect the actuation rod to the yoke (for actuation of the end effector).

SUMMARY OF THE INVENTION

A connector formed from at least two materials for use with a laparoscopic device to interface a tube end with a tip end. The connector includes a rigid base and a seal that are integrally formed to provide a connection between the tube end and the tip end that is electrically insulative and protects against fluid intrusion.

In one embodiment, there is a connector in the form of a laparoscopic instrument tip for interfacing with a laparoscopic tube end, the laparoscopic instrument tip including a base forming a body of the connector, the base being electrically insulative and configured to interface with the tube end and the instrument tip, and a seal integrally formed with the base, the seal having an engagement part on at least one side and expanding upon being engaged.

In one aspect, the engagement part engages with at least one of the tube end and the instrument tip, thereby fluidically sealing and electrically insulating the connection therebetween.

In yet another aspect, the base is rigid and formed as one of a cylindrical shape, circular shape, square shape, rectangular shape and triangular shape.

In another aspect, the integrally formed base and seal are formed as a single component and from different materials. In still another aspect, the seal includes a plastic material encasing a fluid, whereby the fluid is released and acts as an insulative material upon being engaged.

In another aspect, the seal is at least partially destroyed upon being engaged with at least one of the tube end and the instrument tip.

An aspect provides a connector for connecting an instrument tip with a laparoscopic tube end, the connector having a base forming a body of the connector, the base having a lumen configured to accommodate an instrument tip actuator therein, and a seal permanently bonded to an inner surface of a proximal end of the base and configured to deform upon connection of the connector with the tube end.

In a further aspect, when the connector connects to the tube end, the instrument tip actuator is electrically insulated and fluidically sealed from the outside of the tube end. Further, the connector may be unitarily formed with the instrument tip.

In another aspect, the connector can further include an engagement region on at least one of the base and the seal, wherein the engagement region is one of threaded, press-fit, bayonet, ball-and-detent, barrel pin, dog-tooth ratchet mechanism, and the engagement region is configured to engage a complimentary engagement region on the tube end. Further, in a non-limiting aspect, when the connector connects to the tube end, the seal is not visible from the exterior of the connector and tube end.

In yet another aspect, the seal may be chemically bonded to the base by a chemical bonding agent. Also, the base material may be more rigid than the seal material.

In a further aspect, the seal is permanently deformed upon being engaged with the tube end. Also, at least one of the base and seal is one of permanently, dissolved, deformed and destroyed after a predetermined number of uses or predetermined amount of time.

In another aspect, the base includes at least one of a recess and protrusion on the inner surface thereof, and the seal is permanently mechanically bonded to the at least one of the recess and protrusion.

In yet another aspect, a distal end of the base is configured to removably attach to a proximal end of the instrument tip. Also, the distal end of the base may be configured to removably threadably attach to the proximal end of the instrument tip.

In still another aspect, the seal proximally extends from the base when the connector is unattached to the tube end, and the base fits flush against the tube end when the connector is attached to the tube end. In a further aspect, an outer diameter of the seal extends radially outwardly beyond an inner diameter of the base when the connector is unattached to the tube end, and the outer diameter of the seal is within the inner diameter of the base when the connector is attached to the tube end.

Also, an outer diameter of the seal may be less than an outer diameter of the base.

In a further aspect, at least one of the base and seal at least one of deforms, degrades and dissolves when exposed to chemical or heat sterilization.

In another aspect, provided is a laparoscopic device, including a tube end having an outer tube end and an inner shaft, an instrument tip configured to engage with the tube end, and a connector having a base and seal, the seal having an engagement part on at least one side and expanding upon being engaged with at least one of the tube end and the tip end.

In a further aspect, provided is a laparoscopic device, having a tube having a lumen and a slidable inner shaft, an instrument tip configured to be affixed to a distal end of the tube, and a connector affixed to a proximal end of the instrument tip having a back hub and seal permanently bonded to the back hub, the seal configured to deform upon engaging the tube.

In an additional aspect, the instrument tip and the connector are unitarily formed together. Also, the tube may electrically insulate and fluidically seals the inner shaft from the outside of the tube end.

In another aspect, the back hub is one of threaded, press-fit, bayonet, ball-and-detent, barrel pin, dog-tooth ratchet mechanism. Also, the seal may include at least one fluid-encased pocket, wherein upon deformation of the at least a portion of the seal, the pocket is ruptured and fluid is released. Further, the seal may be at least partially visible when the connector is connected to the tube.

In yet another aspect, at least one of the back hub and seal is one of permanently deformed, dissolved and destroyed after a predetermined number of uses or predetermined amount of time.

In another aspect, the base is rigid and formed as one of a cylindrical shape, circular shape, square shape, rectangular shape and triangular shape.

In still another aspect, the integrally formed base and seal are formed as a single component and from different materials.

In another aspect, the seal includes a plastic material encasing a fluid, whereby the fluid is released and acts as an insulative material upon being engaged. The seal may include at least one fluid-encased pocket, wherein upon deformation of the at least a portion of the seal, the pocket is ruptured and fluid is released.

In still another aspect, the seal is at least partially visible when the connector is interfaced with at least one of the tube end and instrument tip.

In another aspect, the seal is at least partially destroyed upon being engaged with at least one of the tube end and the instrument tip.

According to a further aspect, provided is a connector for connecting an instrument tip with a laparoscopic tube end, the connector having a base forming a body of the connector, the base having a lumen configured to accommodate an instrument tip actuator therein, and a seal configured to deform upon connection of the connector with the tube end, wherein the base and seal are formed of a single unitary material, and wherein one of the base and seal are subject to one of chemical, optical and radiological exposure, such that the seal is more flexible than the base.

Another feature of the invention provides an instrument tip configured to be connected to a tube end, the instrument tip having a back hub having a hollow center configured to accommodate an end effector actuator therein, an end effector configured to engage a target, wherein the end effector actuator configured to actuate the end effector, and an elastomeric seal permanently bonded to an inner surface of the back hub and configured to deform upon connection of the connector with the tube end.

According to another aspect, the end effector actuator is a yoke configured to mechanically actuate the end effector, and a proximal end of the yoke is configured to attach to an axially slidable rod located in the tube end.

According to another aspect, the back hub comprises threading on an inside surface thereof, the threading configured to engage complimentary threading on the tube end, the end effector actuator is a yoke configured to mechanically actuate the end effector, and a proximal end of the yoke includes yoke threading configured to threadably attach to complimentary threading on an axially slidable rod located in the tube end.

According to a further aspect, the back hub includes at least one of a recess and protrusion on the inner surface thereof, and the seal is permanently mechanically bonded to the at least one of the recess and protrusion. Additionally, the seal may be chemically bonded to the base by a chemical bonding agent.

Also provided is a method of forming a connector configured to attach to a tube end, the method including molding a connector base having a hollow center and at least one of a recess and protrusion on the inner surface of the connector base, placing the connector base inside a mold, extruding liquid silicon material into the mold such that the liquid silicon material permanently mechanically bonds to the at least one of a recess and protrusion, to form a seal on a proximal end of the connector base, upon curing of the silicon material.

Further provided is a method of forming a connector configured to attach to a tube end, the method including, molding a connector base having a hollow center, placing the connector base inside a mold, and extruding liquid silicon material and a bonding agent into the mold such that the liquid silicon material permanently chemically bonds to an inner surface of the connector base to form a seal on a proximal end of the connector base, upon curing of the silicon material.

DETAILED DESCRIPTION

Figure 1:
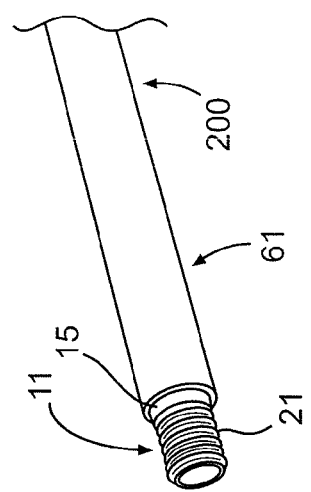
FIG. 1 shows a perspective view of an end of a reusable handpiece with a conventional seal.
Figure 1:
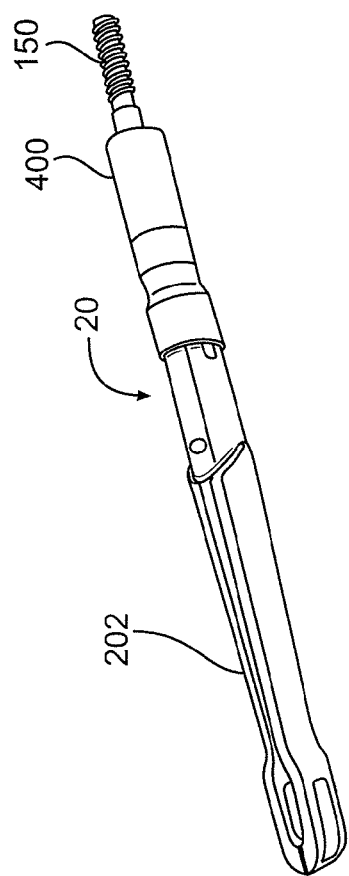

The particulars shown herein are by way of example and for purposes of illustrative discussion of the embodiments of the present invention only, and are presented for providing what is believed to be the most useful and readily understood description of the principles and conceptual aspects of the present invention. In this regard, no attempt is made to show structural details of the present invention in more detail than is necessary for the fundamental understanding of the present invention, the description taken with the drawings making apparent to those skilled in the art how the several forms of the present invention may be embodied in practice.

FIGS. 4-7 show an exemplary embodiment of a connector of a laparoscopic instrument tip in accordance with a non-limiting aspect of the disclosure. A laparoscopic instrument tip 500 is attachable to a reusable handpiece 200 (described in relation to FIGS. 1-2) and is used for performing a minimally-invasive laparoscopic procedure such as excision of tissue with cauterization. The tip 500 may typically include (but is not limited to) a tip 500 having an end effector 505 (which may or may not be electrified) such as a grasper, ligation tool, blade, shears, a cauterization tool and the like, in which the tip 500 may engage with the tube end 11 of a tube 61 which extends from a base portion connected to handles (or other suitable control device, not shown) operable by the medical personnel or physician performing the surgery.

Figure 7:
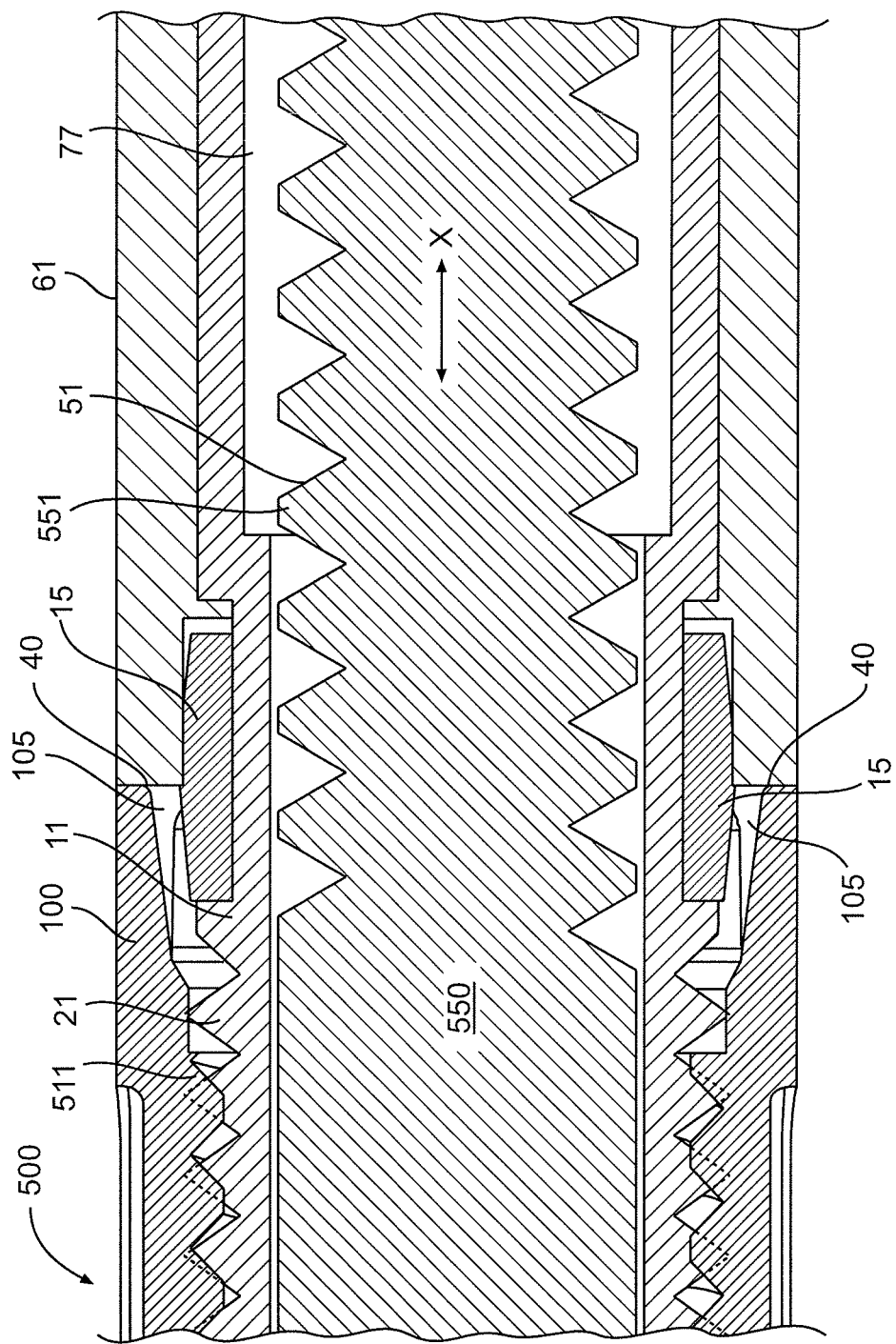
FIG. 7 shows a side sectional view of the connector in accordance with a non-limiting aspect of the disclosure connected to a laparoscopic tube end.

As best shown in FIG. 7, the tip 500 includes a tip actuator in the form of, e.g., a yoke 550 having external threading 551, which engages complementary internal threading 51 on an actuation rod 77 extending along the length of the tube 61 and slidable in direction X relative to the tube (thereby providing for the actuation of the end effector), and the connector 100 includes internal threading 511 which engages the complimentary external threading 21 on the tube end 11 to secure the connector 100 to the tube 61. In this embodiment, the connector 100 serves as a back hub and may also be termed as such herein. Although the figures show the connector 100 connecting the tip to the tube 61 using the above-described a dual-threaded attachment mechanism, those skilled in the art will appreciate that a single-threaded (or no-threaded) attachment mechanism may be employed. In a single-threaded attachment arrangement, while the connector 100 includes internal threading 511 which engages the complimentary external threading 21 on the tube end 11, the yoke 550 and actuation rod 77 can connect by other mechanisms, including but not limited to press-fit, bayonet, ball-and-detent, barrel pin, dog-tooth ratchet mechanism and the like. In a no-threaded attachment mechanism, the connector 100 may not employ a threaded design. As an alternative to internal threading 511 which engages the complimentary external threading 21 on the tube end 11, the connector may employ any form of any suitable engagement technology including but not limited to press-fit, bayonet, ball-and-detent, barrel pin, dog-tooth ratchet mechanism and the like. It is also noted that while the tip actuator is shown as a yoke 550 configured to move in the X direction relative to the tube 61, those skilled in the art will appreciate that the tip actuator need not move (e.g., in the event that the end effector is stationary).

Figure 5:
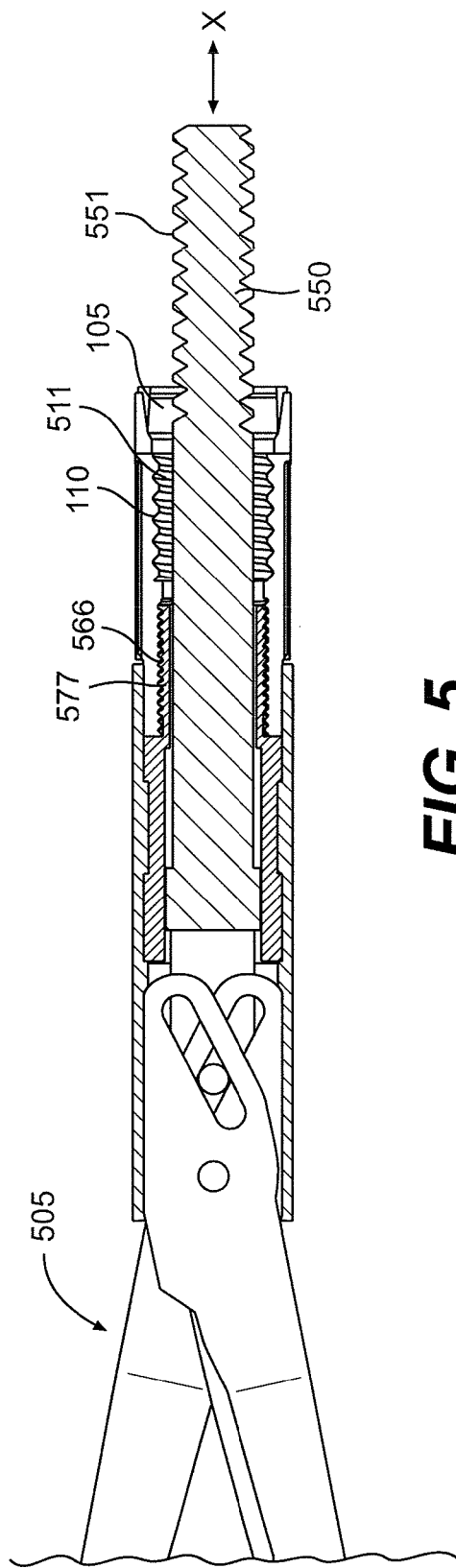
FIG. 5 shows a side sectional view of the connector and instrument tip of FIG. 4.

The connector 100 includes seal 105 (discussed below) and according to a non-limiting aspect, is threadedly affixed to the tip 500. For example and as shown in FIG. 5, the distal end of the connector 100 my include internal threading 566 to threadedly engage external threading 577 on the proximal end of the tip 500, although those skilled in the art will appreciate that the connector may have the external threading and the tip may have the internal threading. Although the figures show the connector 100 threadedly attached to the tip 500, those skilled in the art will also appreciate that the connector and tip may be connected by other means (including but not limited to press-fit, bayonet, ball-and-detent, barrel pin, dog-tooth ratchet mechanism and the like), and that the connector and cylindrical tip portion may be unitarily formed from a single piece of material.

Figure 6:
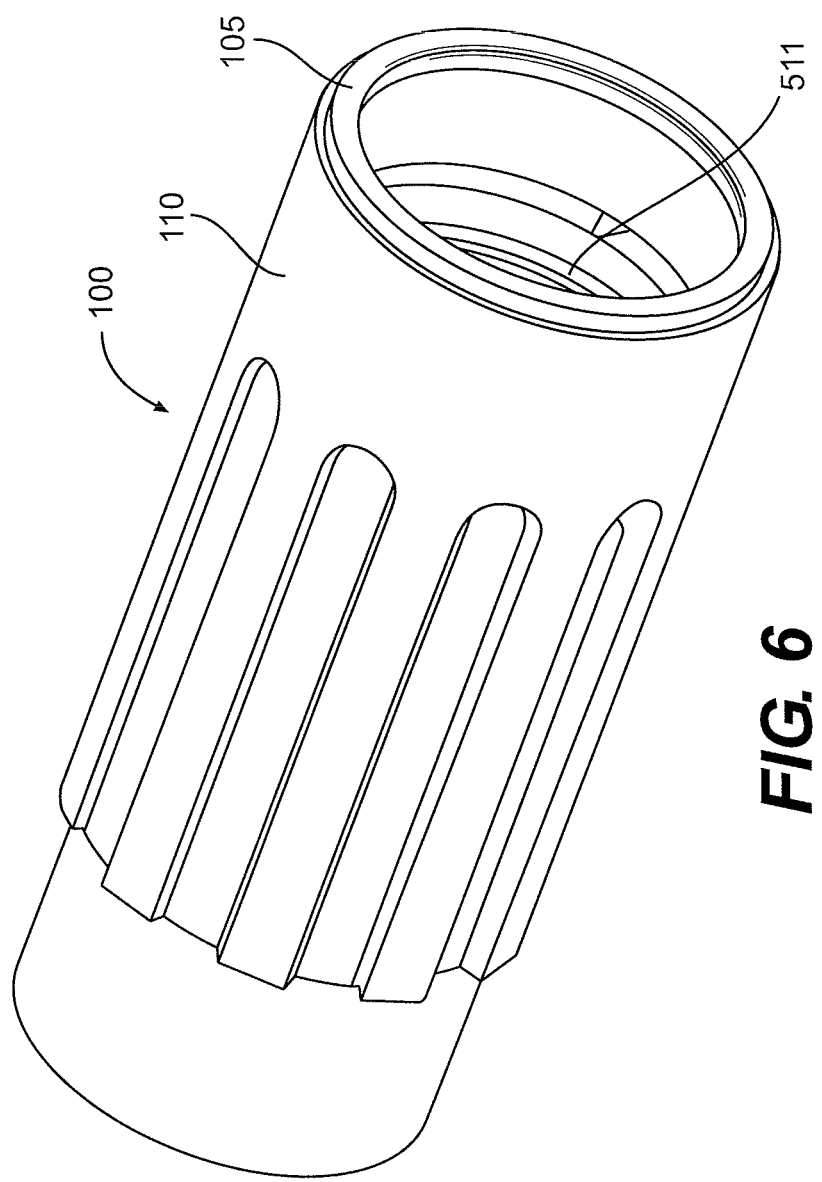
FIG. 6 shows a perspective view of the connector in accordance with a non-limiting aspect of the disclosure.

FIG. 6 shows an exemplary embodiment of the connector 100. The connector 100, as illustrated, shows an elastomeric seal 105 provided in a cylindrically-shaped base 110 (i.e., the portion of the connector other than the seal) made of a material that is more rigid that the material of which the seal is formed. According to a feature of the disclosure, when using mechanical bonding (mechanical interlocking) between the seal 105 and the base 110, the base is formed from polyphenylsulfone (PPSU)(commonly referred to by the trade name Radel®), or may be formed from Polysulphone (PSU)(commonly referred to by the trade name Udel®), although those skilled in the art would appreciate that any suitable mid-range or higher polymer may be used.

According to a feature of the disclosure, the seal 105 is formed from a flexible material such as silicone, although those skilled in the art would appreciate that any suitable flexible material may be used. For a chemically-bonded connection between the seal 105 and the base 110, the exact material of the base 110 and of the seal 105 may be selected based on the type adhesive in the silicone. It is noted that the base 110 or seal 105 may be constructed of material that deforms, degrades or dissolves when exposed to chemical or heat (e.g., autoclaving) sterilization. In this way, the tip 500 is prevented from being reused.

The seal 105 may be unitarily formed (from a single piece of material) with the base 110 or may be formed separate from the base 110, as explained below. Likewise, base 110 need not be made of a rigid material, but may provide for an acceptable degree of flexibility, so long as the base is more rigid than the seal 105. In this regard, the connector 100 includes at least two materials which together form a single component. This integration allows the selection of materials for the base 110 and seal 105 to have mutually exclusive requirements. In a non-limiting aspect, the connector 100 is formed to be strong, rigid and electrically insulative, while at the same time creating a compliant connection (in the form of the seal 105) that protects against fluid intrusion. It is appreciated that the connector 100 may be formed in any suitable shape, and is not limited to the specific shape disclosed in the drawings.

Although the figures show the length of seal 105 only partially extending inside the base 110 in the X direction, it is appreciated by those skilled in the art that the seal may be of any suitable length in the X direction (including extending the entire length of the base 110). In this regard, while the figures show the internal threading 511 is being formed of the same rigid material as the base, it is appreciated by those skilled in the art that the seal 105 may also include the internal threading.

Figure 2:
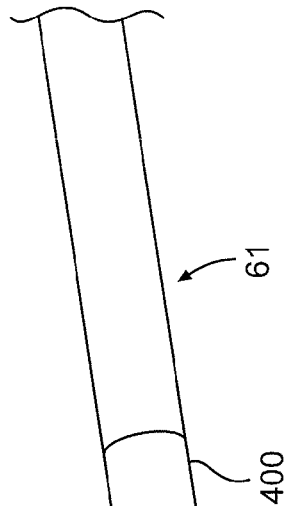
FIG. 2 shows a perspective view of an assembled embodiment of a laparoscopic surgical tip of FIG. 1.
Figure 2:
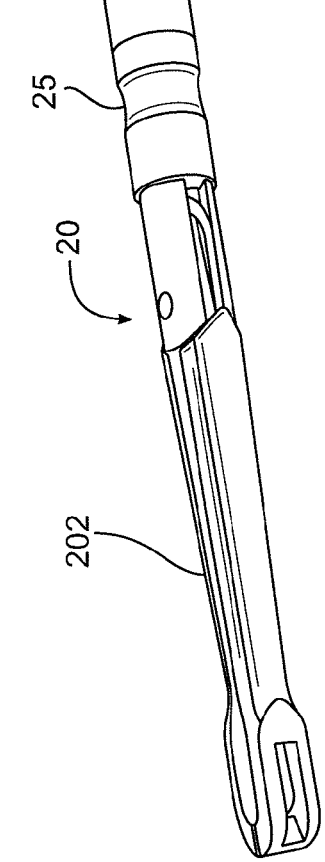
Figure 3:
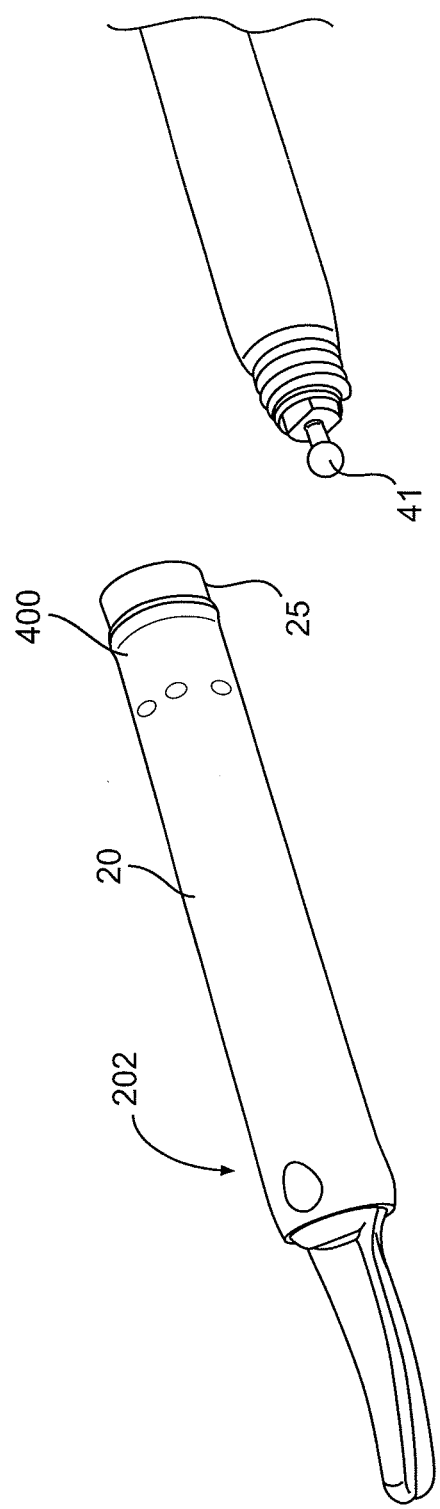
FIG. 3 shows a perspective view of a prior art laparoscopic device in which a piece of flared heart shrink is used on a disposable tip to create a seal to the handpiece.

The seal 105 of the connector 100 either supports (supplements) or replaces, for example, the function of the tube end seal 15 on the reusable handpiece illustrated in FIG. 1. The connector 100 may be rigid and electrically insulative, or may be either entirely or partially formed of an elastomeric material including, but not limited to, for example, natural or artificial rubber, plastic (such as, for example, polyethylene, polypropylene, PPSU, PSU or any other suitable plastic polymer), and/or resin (and/or any suitable mixture or compound thereof, noting that the elastomeric material is not limited to the exemplary materials thus noted). Further, the seal 105 may be formed from a different material than the base 110, at one or both ends that may be unitarily integrated into the base 110 to form the connector 100. The seal 105 may also be formed such that it is not unitarily formed with the base 110, but rather formed separately and bonded to the base 110.

Figure 4:
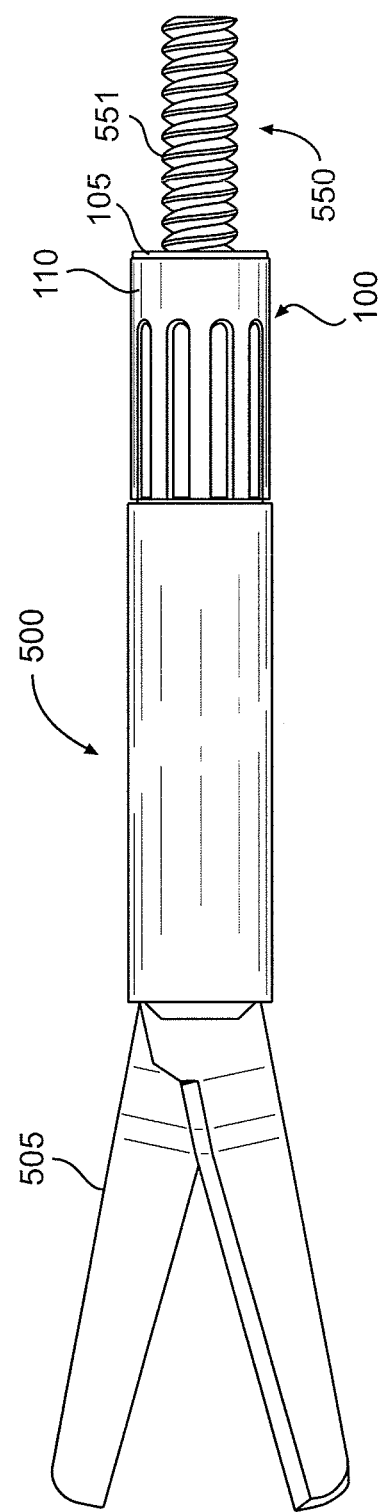
FIG. 4 shows a side elevational view of an exemplary embodiment of a connector for an instrument tip in accordance with a non-limiting aspect of the disclosure.

As shown in FIG. 4, in the unattached state, the seal 105 proximally extends past the base 110 in the X direction, and (as shown in FIGS. 4-5) the outer diameter of the seal further extends radially outwardly beyond the inner diameter of the base. As shown in FIG. 7, the connector 100 is threadedly attached to the tube end 11, the seal 105 deforms against the distalmost portion of the tube 61 (flange 40) and if forced radially inwardly toward the outside of the tube end seal 15, such that the seal 105 no longer proximally extends past the base 110 in the X direction or extends radially outwardly beyond the inner diameter of the base, so that the outer diameter of the assembled device is not interrupted by the seal. As such and as shown in FIG. 7, when attached, the connector abuts flush directly against the distalmost portion of the tube 61 at the tube end 11. In the event that during attachment of the tip 500 to the tube 61 end and the seal 105 is visible to the user, the user may note that there is an error in attaching the tip 500 to the tube 61, and that the tip should be reattached or a different tip should be used. To this effect, the seal 105 may be of a color contrasting with the colors of the connector 100 and tube 61. It is preferred that the connector 100, tip 500 and tube 61 have the same outer diameter for ease of operation.

The ability of the connector 100 to conform to the handpiece 200 offers additional sealing redundancy at the junction when used in conjunction with other sealing members, such as the tube end seal 15 (although it is noted that the seal 105 may replace the tube end seal). This redundancy allows a handpiece 200 to be used safely, regardless of the tube end seal 15 condition. It is appreciated that the connector 100 may be formed in any desired shape, and is not limited to the specific embodiments disclosed in the drawings.

This attachment of the tip 500 to the tube 61 as shown in FIG. 7 seals the interior of the laparoscopic tube end 11 (i.e., the cavity where the yoke 550 and rod 77 operate) from any fluids surrounding the tip 500 or tube end 11, and electrically insulates and fluidically isolates the laparoscopic tube end 11 from the exterior of the tube 61 and tip 500 because the pressure between the distalmost portion of the tube 61 (flange 40) and seal 105 and the adhesiveness and elasticity of the seal 105 form a fluidic seal, and the electrically insulating properties of the elastomeric material of the seal 105 form a high electrical impedance. In addition, the pressure of the seal 105 in the connector 100, when fully engaged against the flange 40, may beneficially prevent rotation and/or disengagement of the connector 100 from the laparoscopic tube end 11, because the frictional resistance resulting from the abutment of the seal 105 of the connector 100 against the flange 40 tends to prevent rotation and unscrewing of the connector 100 from the tube end 11. The composition, shape and/or materials of the seal 105 and/or connector 100 may be selected to optimize the frictional contact with the seal 105, the effectiveness of the fluidic seal, and/or the effectiveness of the electrical impedance thereof, for example.

In accordance with a non-limiting feature, the connector 100 is formed using an insert molding process. In such a process, the formed base 110 is inserted into a mold, whereupon the seal material (e.g., silicone) is extruded into the mold and bonded to the base to create the connector. The seal 105 may be chemically and/or mechanically bonded to the base 110. In the case of chemical bonding, the seal material, combined with a chemical bonding agent (e.g., an adhesion promoter), is extruded into the mold, whereupon during the curing process, the seal 105 permanently and chemically bonds to the base 110 and cannot be removed from the base without destroying the connector 100.

In the case of mechanical bonding, the portion of inside of the base 110 to interface with the seal 105 includes one or more recesses (e.g., a recessed channel), one or more protrusions or a combination thereof for accepting the seal material therein. The seal material (without a chemical bonding agent) is then extruded into the mold and extrudes into the recess(es) and/or over protrusion(s) and then cures. The action of molding the seal 105 in place creates a mechanically-integrated, permanently-bonded component (connector 100) which has two sets of material properties. The recess/protrusion combination increases the surface area of the inside of the base 110 for contacting the seal 105, and as such, removal of the seal from the base cannot be done without destroying the connector 100. It will also be appreciated that a combination of chemical and mechanical bonding between the seal 105 and base 110 can be performed.

In accordance with another non-limiting feature, the connector 100 is formed using an double molding process. In this process, a primary molding material (base 110) is first poured in a mold. After the primary molding (base 110) is formed, a secondary molding material (seal 105) poured is added to the same mold to form a composite, double-molded connector. It is noted that the above-described chemical and/or mechanical bonding process may be used in the double-molding process.

In accordance with a further non-limiting embodiment, the seal 105 includes a flexible material (such as a flexible ring) that may separately formed from the base 110 (e.g., by molding) and then inserted or placed into the base 110 to form the connector 100. In this embodiment, the connector 100 is formed of the base 110 and seal 105, without the seal having to be bonded or unitarily formed with the base into the connector 100.

Figure 8:
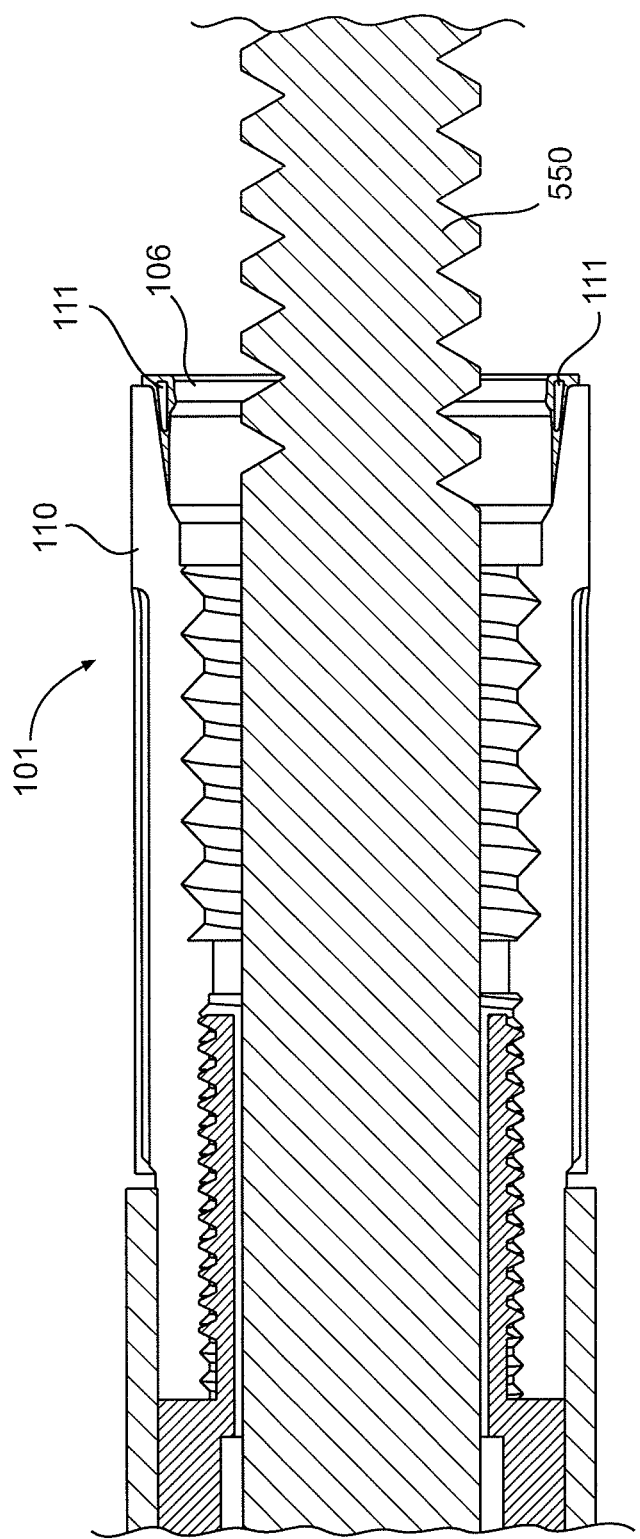
FIG. 8 shows a side sectional view of the connector in accordance with a second non-limiting embodiment.

FIG. 8 shows another embodiment of a connector 101, in which a seal 106 includes one or more pockets 111 encasing a viscous fluid. Once compressed, pressure from the compression results in the pocket(s) being breached or ruptured, releasing a fluid (including but not limited to a silicone fluid) inside the connector 101. In other words, upon assembly of the connector 101 with the tube 61, the fluid is compressed out of the pocket(s) 111 to flood any clearances left in the connector-tube junction. The released fluid may act as an additional insulation material. Further, since the breached pockets alter the dimensions of the seal, re-use of the tip 500 is further prevented.

In additional embodiments, the seal 105 can be fully or partially visible to the user (and may be of contrasting color to the base 110 and tube 61), thereby providing visual confirmation of the tip's 500 proper installation. The seal 105 may also be designed for a single application to the tube end 11 such that the seal 105 can get partially or fully dissolved, deformed or destroyed upon use (or multiple uses, fixed or otherwise), thereby preventing the tip 500 from being re-used. In other words, the inner material of the seal 105 may be configured such that once the outer surface of the tube end 11 (e.g., threading 21) engages the inner material of the seal (e.g., complementary threading 511) to attach the tip 500 to the tube 61, the inner material is permanently deformed such that upon disengagement of the tube end and the tip, the tube end and the tip cannot be securely (i.e., successfully enough for the instrument 65 to be used in a medical procedure) reattached. In this way, the tip 500 is prevented from being reused.

Figure 9:
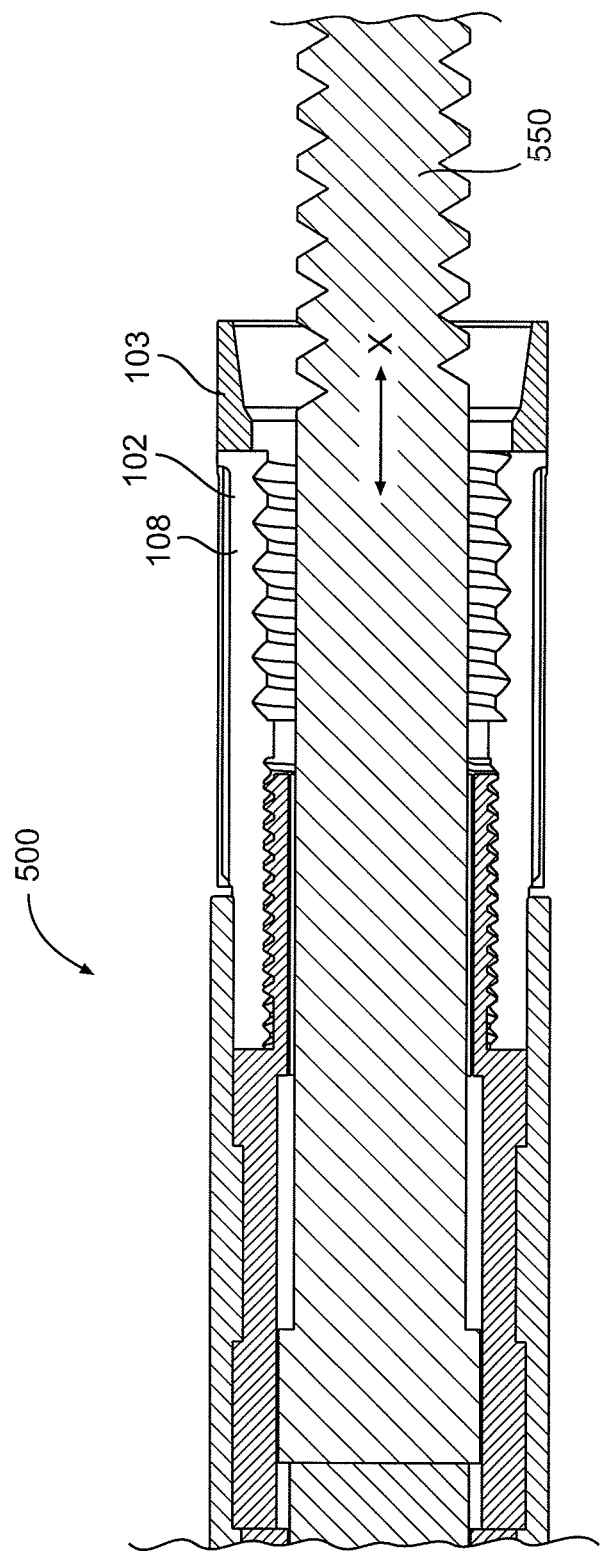
FIG. 9 shows a side sectional view of the connector in accordance with a third non-limiting embodiment.

FIG. 9 shows a connector 102 according to a further embodiment. Rather than providing a connector 100 including at least two materials bonded to form a single component as described above a connector 102 is formed of a single unitary type of material, a portion of which is treated to alter the material properties thereof, such that the connector has two different elastomeric properties at respectively two different regions in the X direction. In other words, a portion of the connector 102 is treated chemically (via application of a chemical), optically (via application of light) or radiologically (via application of radiation) to render the portion harder or softer than the remainder (untreated portion) of the connector 102. As an example, if the connector 102 is formed of PTFE (Polytetrafluoroethylene), and a portion 108 is irradiated, this portion 108 will become hard (harder than the non-irradiated portion 103, which can then serve as the seal). It is noted that such treatment of the connector can be performed before or after the tip 500 is attached to the tube 61.

In view of the foregoing, the present disclosure, through one or more of its various aspects, embodiments and/or specific features or sub-components, is thus intended to bring out one or more of the advantages as specifically noted below. While the present disclosure includes description with respect to a medical device and procedure, the present invention may be used in a variety of other, non-medical, environments.

The illustrations of the embodiments described herein are intended to provide a general understanding of the structure of the various embodiments. The illustrations are not intended to serve as a complete description of all of the elements and features of apparatus and systems that utilize the structures or methods described herein. Many other embodiments may be apparent to those of skill in the art upon reviewing the disclosure. Other embodiments may be utilized and derived from the disclosure, such that structural and logical substitutions and changes may be made without departing from the scope of the disclosure. Additionally, the illustrations are merely representational and may not be drawn to scale. Certain proportions within the illustrations may be exaggerated, while other proportions may be minimized. Accordingly, the disclosure and the figures are to be regarded as illustrative rather than restrictive.

One or more embodiments of the disclosure may be referred to herein, individually and/or collectively, by the term "invention" merely for convenience and without intending to voluntarily limit the scope of this application to any particular invention or inventive concept. Moreover, although specific embodiments have been illustrated and described herein, it should be appreciated that any subsequent arrangement designed to achieve the same or similar purpose may be substituted for the specific embodiments shown. This disclosure is intended to cover any and all subsequent adaptations or variations of various embodiments. Combinations of the above embodiments, and other embodiments not specifically described herein, will be apparent to those of skill in the art upon reviewing the description.

The Abstract of the Disclosure is submitted with the understanding that it will not be used to interpret or limit the scope or meaning of the claims. In addition, in the foregoing Detailed Description, various features may be grouped together or described in a single embodiment for the purpose of streamlining the disclosure. This disclosure is not to be interpreted as reflecting an intention that the claimed embodiments require more features than are expressly recited in each claim. Rather, as the following claims reflect, inventive subject matter may be directed to less than all of the features of any of the disclosed embodiments. Thus, the following claims are incorporated into the Detailed Description, with each claim standing on its own as defining separately claimed subject matter.

The above disclosed subject matter is to be considered illustrative, and not restrictive, and the appended claims are intended to cover all such modifications, enhancements, and other embodiments which fall within the true spirit and scope of the present disclosure. Thus, to the maximum extent allowed by law, the scope of the present disclosure is to be determined by the broadest permissible interpretation of the following claims and their equivalents, and shall not be restricted or limited by the foregoing detailed description.

What is claimed is:

1. A connector for connecting an instrument tip with a laparoscopic tube end, the connector comprising:
   a base forming a body of the connector, the base having a lumen configured to accommodate an instrument tip actuator therein; and
   a seal permanently and chemically bond molded to an inner surface of a proximal most end of the base and configured to deform upon connection of the connector with the tube end such that upon disengagement of the connector and the tube end, the seal is deformed such that the tube end and the tip cannot be securely reattached.

2. The connector of claim 1, wherein when the connector connects to the tube end, the instrument tip actuator is electrically insulated and fluidically sealed from the outside of the tube end.

3. The connector of claim 1, further comprising an engagement region on at least one of the base and the seal, wherein:
the engagement region is one of threaded, press-fit, bayonet, ball-and-detent, barrel pin, dog-tooth ratchet mechanism, and
the engagement region is configured to engage a complimentary engagement region on the tube end.

4. The connector of claim 1, wherein when the connector connects to the tube end, the seal is not visible from the exterior of the connector and tube end.

5. The connector of claim 1, wherein the seal comprises at least one fluid-encased pocket, wherein upon deformation of at least a portion of the seal, the pocket is ruptured and fluid is released.

6. The connector of claim 1, wherein the seal is permanently deformed upon being engaged with the tube end.

7. The connector of claim 1, wherein at least one of the base and seal is one of permanently dissolved, deformed and destroyed after a predetermined number of uses or predetermined amount of time.

8. The connector of claim 1, wherein the base material is more rigid than the seal material.

9. The connector of claim 1, wherein a distal end of the base is configured to removably attach to a proximal end of the instrument tip.

10. The connector of claim 9, wherein the distal end of the base is configured to removably threadably attach to the proximal end of the instrument tip.

11. The connector of claim 1, wherein:
the seal proximally extends from the base when the connector is unattached to the tube end; and
the base fits flush against the tube end when the connector is attached to the tube end.

12. The connector of claim 1, wherein an outer diameter of the seal is less than an outer diameter of the base.

13. The connector of claim 1, wherein at least one of the base and seal at least one of deforms, degrades and dissolves when exposed to chemical or heat sterilization.

14. The connector of claim 1, wherein:
an outer diameter of the seal extends radially outwardly beyond an inner diameter of the base when the connector is unattached to the tube end; and
the outer diameter of the seal is entirely within the inner diameter of the base when the connector is attached to the tube end.

15. The connector of claim 1, wherein:
the base comprises internal threading; and
the seal is permanently bonded to the inner surface of the base at a position proximal to the internal threading.

16. The connector of claim 1, wherein the seal proximally protrudes from the proximal most end of the base.

17. The connector of claim 1, wherein the seal is of a color contrasting with a color of the base.

18. The connector of claim 1, wherein the seal is permanently, adhesively and chemically bond molded to the inner surface of the proximal most end of the base.

19. A connector for connecting an instrument tip with a laparoscopic tube end, the connector comprising:
a base forming a body of the connector, the base having a lumen configured to accommodate an instrument tip actuator therein, the base comprising at least one of a recess and protrusion on the inner surface of a proximal most end of the base; and
a seal permanently mechanically bond molded to the at least one of the recess and protrusion, wherein the seal is configured to deform upon connection of the connector with the tube end, such that upon disengagement of the connector and the tube end, the seal is deformed such that the tube end and the tip cannot be securely reattached.

20. A laparoscopic device, comprising:
a tube having a lumen and a slidable inner shaft;
an instrument tip configured to be affixed to a distal end of the tube; and
a connector affixed to a proximal end of the instrument tip having a back hub and seal permanently bonded to the back hub, the seal configured to deform upon engaging the tube such that upon disengagement of the connector and the tube, the seal is deformed such that the tube and the tip cannot be securely reattached.

21. The laparoscopic device of claim 20, wherein the instrument tip and the connector are unitarily formed together.

22. The laparoscopic device of claim 21, wherein the tube electrically insulates and fluidically seals the inner shaft from the outside of the tube end.

23. The laparoscopic device of claim 20, wherein the back hub is one of threaded, press-fit, bayonet, ball-and-detent, barrel pin, dog-tooth ratchet mechanism.

24. The laparoscopic device of claim 20, wherein the seal includes at least one fluid-encased pocket, wherein upon deformation of the at least a portion of the seal, the pocket is ruptured and fluid is released.

25. The laparoscopic device of claim 20, wherein the seal is at least partially visible when the connector is connected to the tube.

26. The laparoscopic device of claim 20, wherein at least one of the back hub and seal is one of permanently deformed, dissolved and destroyed after a predetermined number of uses or predetermined amount of time.

27. The laparoscopic device of claim 20, wherein the back hub material is more rigid than the seal material.

28. A connector for connecting an instrument tip with a laparoscopic tube end, the connector comprising:
a base forming a body of the connector, the base having a lumen configured to accommodate an instrument tip actuator therein; and
a seal configured to deform upon connection of the connector with the tube end such that upon disengagement of the connector and the tube end, the seal is deformed such that the tube end and the tip cannot be securely reattached,
wherein: the base and seal are formed of a single material, and the seal is more flexible than the base.

29. An instrument tip configured to be connected to a tube end, the instrument tip comprising:
a back hub having a hollow center configured to accommodate an end effector actuator therein;
an end effector configured to engage a target, wherein the end effector actuator configured to actuate the end effector; and
an elastomeric seal permanently bonded to an inner surface of the back hub and configured to deform upon connection of the connector with the tube end such that upon disengagement of the connector and the tube end, the seal is deformed such that the tube end and the tip cannot be securely reattached.

30. The instrument tip of claim 29, wherein:
the end effector actuator is a yoke configured to mechanically actuate the end effector, and
a proximal end of the yoke is configured to attach to an axially slidable rod located in the tube end.

31. The instrument tip of claim 29, wherein:
the back hub comprises threading on an inside surface thereof, the threading configured to engage complimentary threading on the tube end;
the end effector actuator is a yoke configured to mechanically actuate the end effector, and
a proximal end of the yoke comprises yoke threading configured to threadably attach to complimentary threading on an axially slidable rod located in the tube end.

32. The instrument tip of claim 29, wherein:
the back hub comprises at least one of a recess and protrusion on the inner surface thereof; and
the seal is permanently mechanically bonded to the at least one of the recess and protrusion.

33. The instrument tip of claim 29, wherein the seal is chemically bonded to the base by a chemical bonding agent.

* * * * *